US012663866B2

(12) United States Patent
Tucker et al.

(10) Patent No.: US 12,663,866 B2
(45) Date of Patent: Jun. 23, 2026

(54) METHOD FOR BAYESIAN SUPER-RESOLUTION OF ELECTROENCEPHALOGRAPHIC SOURCE ANALYSIS AND TRANSCRANIAL ELECTRICAL STIMULATION

(71) Applicant: Brain Electrophysiology Laboratory Company, LLC, Eugene, OR (US)

(72) Inventors: Don M. Tucker, Eugene, OR (US); Phan Luu, Eugene, OR (US); Roman Shusterman, Lake Oswego, OR (US); Mariano Fernandez Corazza, Manuel B Gonnet (AR)

( * ) Notice: Subject to any disclaimer, the term of this patent is extended or adjusted under 35 U.S.C. 154(b) by 0 days.

(21) Appl. No.: 19/097,519

(22) Filed: Apr. 1, 2025

(65) Prior Publication Data

US 2025/0231620 A1     Jul. 17, 2025

Related U.S. Application Data

(60) Provisional application No. 63/683,938, filed on Aug. 16, 2024.

(51) Int. Cl.
*G06F 3/01*          (2006.01)
*A61B 5/383*        (2021.01)
(52) U.S. Cl.
CPC .............. *G06F 3/015* (2013.01); *A61B 5/383* (2021.01)

(58) Field of Classification Search
CPC ................................ G06F 3/015; A61B 5/383
USPC .......................................................... 345/156
See application file for complete search history.

(56)                References Cited

U.S. PATENT DOCUMENTS

| | | | |
|---|---|---|---|
| 10,357,654 B1 * | 7/2019 | Pilly ...................... | A61B 5/055 |
| 11,786,694 B2 * | 10/2023 | Poltorak .............. | A61B 5/4812 |
| | | | 600/28 |
| 12,016,634 B2 * | 6/2024 | He ........................ | G06N 3/0464 |
| 2014/0323900 A1 * | 10/2014 | Bibian ................... | A61B 5/372 |
| | | | 604/503 |
| 2021/0166577 A1 * | 6/2021 | Hong ................... | A61B 5/7267 |
| 2024/0108272 A1 * | 4/2024 | Hendler ................ | A61B 5/372 |
| 2025/0248636 A1 * | 8/2025 | Rapoport ................ | A61B 5/37 |

* cited by examiner

*Primary Examiner* — Calvin C Ma

(57)                ABSTRACT

A method for achieving super-resolution in localizing electrical fields measured at the head surface with electroencephalography through a generative model of the cerebral cortex that has a very high resolution of cortical surface dipoles constructed from the known properties of human cerebral cortex and adapted to optimize the Bayesian explanation the individual's cortical surface electrical fields. The iterative optimization of the prior (generative) with the posterior (observed) fields with extensive data from extended recordings provides a probabilistic estimation of the individual's functional brain activity that can be used to train artificial neural network approximations of the individual's mental activity.

24 Claims, 1 Drawing Sheet

Steps in Bayesian Super-Resolution

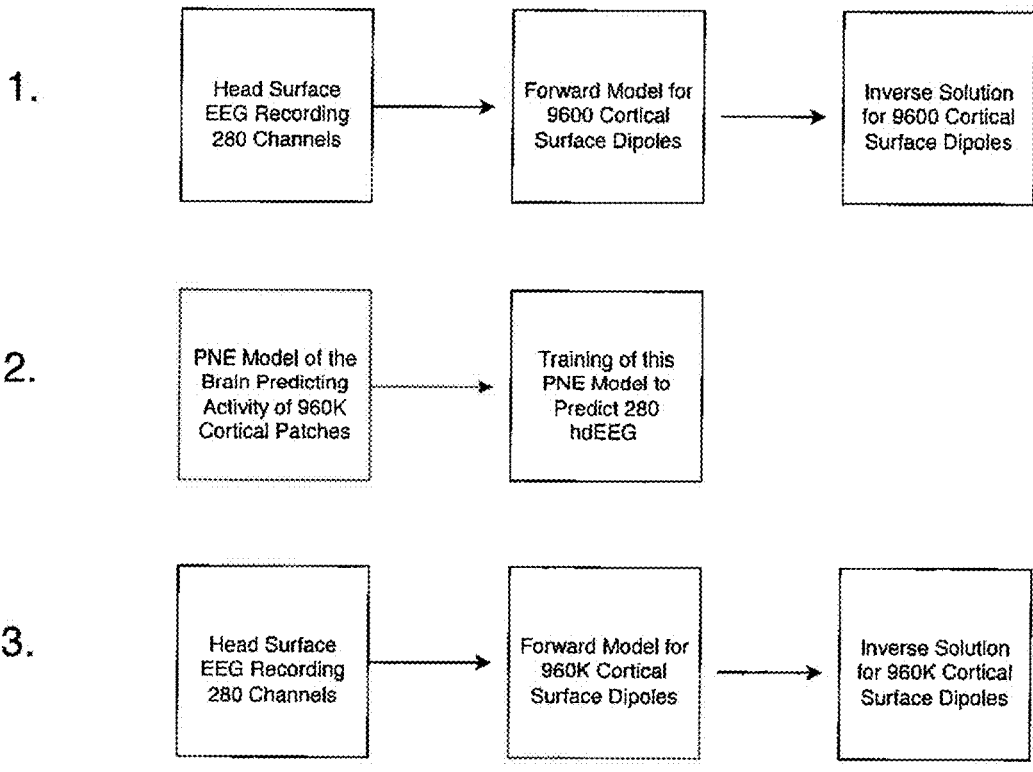
Steps in Bayesian Super-Resolution

METHOD FOR BAYESIAN SUPER-RESOLUTION OF ELECTROENCEPHALOGRAPHIC SOURCE ANALYSIS AND TRANSCRANIAL ELECTRICAL STIMULATION

RELATED APPLICATIONS

The present application claims the benefit of U.S. provisional application Ser. No. 63/683,938, filed Aug. 16, 2024, which is incorporated by reference herein in its entirety.

FIELD OF THE INVENTION

The field of this invention is electrical monitoring (EEG) and modulating (TES) the human brain for the purpose of establishing a brain-computer interface. Specifically, it describes how to achieve super-resolution brain neurophysiology monitoring and modulation using high definition electroencephalography (hdEEG) and iterative Bayesian super-resolution techniques. The result is very-high-definition EEG/TES (vhdEEG/TES), allowing a two-way interface between the human brain and an AI, the Personal Neuromorphic Emulation.

BACKGROUND OF THE INVENTION

Effective brain-computer interfaces (BCIs) are of significant theoretical and practical importance. Traditional EEG has been limited by spatial resolution, typically resolving cortical activity to a resolution of approximately 1 square centimeter (sq cm) on the cortical surface, with a temporal resolution of 1 millisecond (ms). This temporal resolution is easily increased (if physiological monitoring were to require sub-ms resolution), although it is currently assumed that spatial resolution of EEG is inherently poor. However, recent advancements have demonstrated the potential for much higher spatial resolution using dense array (high density) EEG (hdEEG) with advanced source localization techniques. Furthermore, the present method seeks to achieve very high definition EEG (vhdEEG) through Bayesian super-resolution by leveraging a high spatial resolution computational model of brain connectivity and function (Personal Neuromorphic Emulation, PNE).

SUMMARY OF THE INVENTION

The present invention introduces a method for achieving spatial super-resolution in EEG monitoring by integrating a Bayesian prior model of high-resolution brain connectivity and function with hdEEG data. This method aims to estimate the electrical fields at a high spatial resolution (such as down to one cortical macrocolumn per patch) by using dense array or high density hdEEG data (280 or more channels) and advanced Bayesian source localization techniques. The prior model of neuroelectrical activity constructed for the PNE has much higher resolution (~100×) on the surface of the cerebral cortex than the native source estimation (9600 dipoles tessellated over the ~2400 cm² human cerebral cortex) estimated with Multiple Sparse Priors from 280-channel hdEEG (BEL System One). Because this prior model includes the regular and predictable features of neural networks, the higher resolution can constrain the prediction of EEG fields to that predictive resolution, even as the training data is limited to the lower (9600 dipole) resolution. The goal is to achieve a 100× improvement, thereby resolving the electrical activity of one macrocolumn.

Although the actual improvement is only estimated at the present time, the principles can be stated. The more articulate that the PNE becomes (the Bayesian priors of the predictive model) the greater precision of electrical source estimation that can be accomplished. Constraints from prior knowledge strongly shape the prediction of the brain's local electrical fields.

DETAILED DESCRIPTION OF DRAWINGS

FIG. 1: Schematic of iterative source resolution and forward prediction with the PNE. In step 1 the forward model includes only electromagnetic constraints of the individual conductivity head model, plus the minimal constraint that adjacent sources on the cortical surface vary smoothly (no large adjacent deviations). In step 2, the high resolution cortical patch model of the PNE is used as a trusted forward model for predicting the extensive data collected from that individual's 280-channel hdEEG. In step 3 the forward model now includes the anatomy of connectivity, and the trained connection weights, at the 1 macrocolumn super-resolution that predict the large corpus of EEG recordings obtained for that individual.

DETAILED DESCRIPTION OF THE PREFERRED EMBODIMENT

1. High Definition EEG (hdEEG) and Transcranial Electrical Stimulation (hdtES)

The invention utilizes dense array EEG to measure electrical fields generated primarily by cortical neural activity. High definition EEG (hdEEG) allows for source localization at a high resolution. The same principles are used to manipulate neural networks through high definition transcranial Electrical Stimulation (hdtES), optimizing the applied currents based on the head tissue conductivity model.

2. Bayesian Super-Resolution Method

The method begins with a Bayesian prior, a high-resolution computational model of brain connectivity and function (Personal Neuromorphic Emulation or PNE). This model predicts electrical activity at a high resolution (e.g., each cortical patch reflecting ~100 columns). The model is trained to predict hdEEG data, using the lower native resolution of 9600 dipole sources. For a typical 2400 cm² human cortex, assuming roughly 1 million macrocolumns (a macrocolumn contains cortical columns with similar receptive field or functional properties) a tessellation into 9600 patches (each represented by an equivalent dipole) results in ~100 macrocolumns as the native resolution. The high-resolution model of the brain (including cerebral cortex) is then trained to predict the low-resolution 9600-source hdEEG source data through computational modeling of brain activity (with an AI, the Personal Neuromorphic Emulation or PNE) that has a 1 macrocolumn computational "neuron" (a computational unit of an artificial neural network rather than a biological neuron) for its predictive AI model.

It is essential, of course, that the PNE captures the individual's connectional anatomy, such as with high resolution fiber tractography of the individual's brain. This can be first adjusted for accuracy in predicting the original 9600 source activity from extensive hdEEG recordings under varied brain activity conditions (waking behavior and stages of sleep). Furthermore, the PNE's connectivity is articulated at the local level of cortical architecture is gathered from the extensive current neuroscience literature (by a specialized AI, the Neuromorphic Emulation Constructor AI or NECA).

With extensive training of the very-high resolution (1 macrocolumn, 960,000 source) PNE model in predicting the person's low-resolution (9600) source model, the capacity for source resolution of new 280 hdEEG recordings to the 1 microcolumn resolution is obtained.

3. Constructing the Initial Low-Resolution (9600 Source) Cortical Activity Model The initial low-resolution architecture is characterized from structural MRI and diffusion-weighted MRI tractography. These elements create a low-resolution computational model of the brain, analogous to artificial neural networks, with cortical column elements representing stereotyped configurations of processing neurons (in this case computational rather than biological, but closely neuromorphic). The electrical conductivity of head tissues is modeled to allow forward projection of cortical fields, facilitating source inversion from hdEEG data to estimate cortical surface activity.

4. High-Resolution Brain Connectivity Model

The high-resolution brain connectivity model of the preferred embodiment extends the low-resolution model by replacing each of the original 9600 cortical patches with 100 patches of 1 macrocolumn each. This high-resolution model integrates prior knowledge of local cortical anatomy, validated through neuroimaging and anatomical studies.

5. Achieving Bayesian Super-Resolution

The Bayesian estimation fits the high-resolution model to the extensive hdEEG data, source-localized to the the 9600 dipole resolution, collected over extended intervals from the person (weeks and months of data). By constraining the model parameters with anatomical and electrophysiological data, the parameter space is restricted, allowing the lower resolution hdEEG data to train the high-resolution model effectively, particularly with massive data (9600 source localized dipoles) sampled each ms for weeks and months. This results in a very high definition characterization of an individual's cortical activity, estimated with extensive monitoring of that person over time.

6. Modeling Subcortical Controls

While the focus is on cortical activity, subcortical systems are modeled as latent variables, inferred from cortical activity variance. This model considers the stereotyped nature of subcortical systems across individuals. Because the brain has evolved over multiple levels (rhombencephalic, mesencephalic, diencephalic, and multiple reptilian, mammalian, and uniquely human telencephalic), which each of these continuously operative in the human brain, only an evolutionary-developmental construction method is able to capture the hierarchic levels of active inference in the cerebral architecture.

The subcortical control of active inference proceeds as elemental impulses generate structure and dissipate energy. Then constraint of the subcortical inhibitory control limits that structure to more differentiated and validated evidence-based organization. The subcortical control is an essential foundation for order and its evolution in time.

7. Personal Neuromorphic Emulation (PNE)

The PNE integrates the low-resolution brain connectivity model, high-resolution local columnar network model, and subcortical regulatory model. The weights of this integrated model are adjusted to fit long-term hdEEG source-localized data, achieving Bayesian super-resolution and providing a detailed characterization of individual brain function.

The following formulation captures the simple Bayesian mechanics of this estimation process:

Detailed Description of a Preferred Embodiment to a 10× Resolution Increase

1. Forward Problem:

$$E_{EEG} = F(E_{cortex})$$

where F is the forward model that maps the cortical activity $E_{cortex}$ (9600 dipoles) to the EEG measurements $E_{EEG}$ (280 electrodes).

2. Inverse Problem:

The inverse problem is the process of estimating the cortical electrical fields $E_{cortex}$ from the observed EEG measurements $E_{EEG}$.

3. Bayesian Analysis for Inverse Estimation:

Prior Distribution:

$$P(E_{cortex})$$

encapsulates our initial beliefs about the cortical sources before observing the EEG data.

Likelihood Function:

Assuming Gaussian noise, the likelihood can be modeled as:

$$P(E_{EEG}|E_{cortex}) = \mathcal{N}(E_{EEG}; F(E_{cortex}), \sigma^2)$$

Posterior Distribution:

The posterior distribution combines the prior and the likelihood:

$$P(E_{cortex}|E_{EEG}) = \frac{P(E_{EEG}|E_{cortex}) P(E_{cortex})}{P(E_{EEG})}$$

This posterior distribution is the solution to the inverse problem, providing a probabilistic estimate of the cortical sources.

4. Extending to Bayesian Super Resolution:

High-Resolution Model:

Develop a predictive model $M_{high-res}$ that extends the resolution from 9600 to 96,000 cortical sources.

Extended Prior Distribution:

The high-resolution prior:

$$P(E_{high-res})$$

is informed by the posterior estimates from the initial model and extended recordings.

Extended Likelihood Function:

The likelihood for the high-resolution model:

$$P(E_{EEG}|E_{high-res}) = \mathcal{N}(E_{EEG}; F_{high-res}(E_{high-res}), \sigma^2)$$

Here, $F_{high-res}$ is the forward model for the high-resolution cortical sources.

High-Resolution Posterior Distribution:

The posterior distribution for the high-resolution model:

$$P(E_{high-res}|E_{EEG}) = \frac{P(E_{EEG}|E_{high-res})\,P(E_{high-res})}{P(E_{EEG})}$$

This posterior distribution provides a super resolved estimate of the cortical activity, significantly enhancing the spatial resolution beyond the initial model.

Summary of Practical Implementation

1. Initial Inversion:

Perform the Bayesian inversion with the initial model (9600 sources) using EEG data to obtain the posterior:

$$P(E_{cortex}|E_{EEG})$$

2. High-Resolution Prior:

Use the posterior from the initial inversion to inform the high-resolution prior:

$$P(E_{high-res})$$

3. Superresolution Inversion:

Perform the Bayesian inversion with the high-resolution model (96,000 sources) using the same EEG data and the high-resolution prior to obtain the superresolved posterior:

$$P(E_{high-res}|E_{EEG})$$

CONCLUSION

By iteratively refining the predictive model of neuromorphic computational architecture that generates electrical fields from each computational neuron (macrocolumn model) and leveraging detailed priors from extensive recordings, Bayesian analysis allows for the super-resolution of cortical electrical field localization, transforming 280-channel EEG data into highly detailed cortical activity maps with 960,000 sources (each source reflecting representing about 1 macrocolumn). This process achieves a synergistic super-resolution through highly developed predictive modeling, Bayesian inference, and constraint by extensive hdEEG data on the individual brain to achieve unprecedented resolution in brain activity monitoring. This advance in neuroelectric modeling contributes directly to the training of the Personal Neuromorphic Emulation.

BIBLIOGRAPHY

Bastos, A. M., et al. (2012). Canonical microcircuits for predictive coding. Neuron, 76(4), 695-711.

Fernandez-Corazza, M., et al. (2021). Source localization of epileptic spikes using Multiple Sparse Priors. Clinical Neurophysiology, 132(2), 586-597.

Friston, K., et al. (2008). Multiple sparse priors for the M/EEG inverse problem. Neuroimage. 39(3), 1104-1120.

García-Cabezas, M. Á., et al. (2019). The Structural Model: a theory linking connections, plasticity, pathology, development, and evolution of the cerebral cortex. Brain Structure and Function, 224(3), 985-1008.

Li, K., et al. (2016). BrainK for Structural Image Processing: Creating Electrical Models of the Human Head. Comput Intell Neurosci, 2016, 1349851.

Luu, P., et al. (2023). Vertical Integration of Motivational Control Across the Evolved Levels of the Human Neuraxis. Cerebral Cortex.

Marsh, B. M., et al. (2024). Emergent effects of synaptic connectivity on the dynamics of global and local slow waves in a large-scale thalamocortical network model of the human brain. bioRxiv.

Tucker, D. M., & Luu, P. (2021). Motive control of unconscious inference: The limbic base of adaptive Bayes. Neuroscience & Biobehavioral Reviews, 128, 328-345.

The invention claimed is:

1. A method for Bayesian super-resolution of a source localization of a subject's cortical activity measured from EEG data, comprising:

performing a first Bayesian inversion of the EEG data applied on a high-resolution physical model of the subject's head tissue conductivity to obtain a first posterior estimate of the source localization at a high resolution; and employing the first posterior estimate as an extended prior distribution in a second Bayesian inversion of the EEG data applied on a high-resolution computational model of the subject's brain connectivity and function to obtain a second posterior estimate of the source localization at a super-resolution.

2. The method of claim 1, wherein the high-resolution computational model replaces each 100 macrocolumn cortical patch with 100 patches of 1 macrocolumn each.

3. The method of claim 2, further comprising applying transcranial electrical stimulation to the subject's head based on the second posterior estimate of the source localization.

4. The method of claim 1, wherein the high-resolution computational model parameters are constrained by structural MRI and diffusion-weighted MRI tractography data.

5. The method of claim 4, further comprising applying transcranial electrical stimulation to the subject's head based on the second posterior estimate of the source localization.

6. The method of claim 1, further comprising modeling subcortical systems as latent variables inferred from cortical activity variance.

7. The method of claim 6, further comprising applying transcranial electrical stimulation to the subject's head based on the second posterior estimate of the source localization.

8. The method of claim 1, wherein the EEG data are collected at 500-1000 samples/second over weeks or years.

9. The method of claim 8, further comprising applying transcranial electrical stimulation to the subject's head based on the second posterior estimate of the source localization.

10. The method of claim 1, wherein the high-resolution computational model integrates low-resolution brain connectivity, high-resolution local columnar network neurophysiology, and subcortical regulatory models reflecting evolved hierarchic vertical integration of human neural systems.

11. The method of claim 10, further comprising applying transcranial electrical stimulation to the subject's head based on the second posterior estimate of the source localization.

12. The method of claim 1, wherein the high-resolution computational model comprises a PNE.

13. The method of claim 12, wherein the PNE model replaces each 100 macrocolumn cortical patch with 100 patches of 1 macrocolumn each.

14. The method of claim 13, further comprising applying transcranial electrical stimulation to the subject's head based on the second posterior estimate of the source localization.

15. The method of claim 12, wherein the PNE model parameters are constrained by structural MRI and diffusion-weighted MRI tractography data.

16. The method of claim 15, further comprising applying transcranial electrical stimulation to the subject's head based on the second posterior estimate of the source localization.

17. The method of claim 12, further comprising modeling subcortical systems as latent variables inferred from cortical activity variance.

18. The method of claim 17, further comprising applying transcranial electrical stimulation to the subject's head based on the second posterior estimate of the source localization.

19. The method of claim 12, wherein the EEG data are collected at 500-1000 samples/second over weeks or years.

20. The method of claim 19, further comprising applying transcranial electrical stimulation to the subject's head based on the second posterior estimate of the source localization.

21. The method of claim 12, wherein the PNE integrates low-resolution brain connectivity, high-resolution local columnar network neurophysiology, and subcortical regulatory models reflecting evolved hierarchic vertical integration of human neural systems.

22. The method of claim 21, further comprising applying transcranial electrical stimulation to the subject's head based on the second posterior estimate of the source localization.

23. The method of claim 12, further comprising applying transcranial electrical stimulation to the subject's head based on the second posterior estimate of the source localization.

24. The method of claim 1, further comprising applying transcranial electrical stimulation to the subject's head based on the second posterior estimate of the source localization.

\* \* \* \* \*